United States Patent [19]

Wang

[11] Patent Number: 4,813,876

[45] Date of Patent: Mar. 21, 1989

[54] METHOD OF TREATING LIVING PULP TISSUE

[75] Inventor: Wu-Lan Wang, Milford, Del.

[73] Assignee: Dentsply Research & Development Corp., Milford, Del.

[21] Appl. No.: 47,135

[22] Filed: May 8, 1987

Related U.S. Application Data

[62] Division of Ser. No. 696,193, Jan. 29, 1985.

[51] Int. Cl.[4] .......................... A61K 6/08; C08F 2/50; C08F 20/36; C08K 3/22
[52] U.S. Cl. ...................... 433/224; 522/28; 522/82; 522/83; 522/96; 523/116; 524/779; 623/16
[58] Field of Search ................ 522/83; 523/116; 433/200, 228.1, 226, 224

[56] References Cited

U.S. PATENT DOCUMENTS

| | | |
|---|---|---|
| 2,877,199 | 3/1959 | Taub . |
| 3,709,866 | 1/1973 | Waller . |
| 4,089,763 | 5/1978 | Dart ..................... 522/908 |
| 4,243,578 | 1/1981 | O'Sullivan et al. . |
| 4,459,193 | 7/1984 | Ratcliffe .................. 522/908 |
| 4,551,486 | 11/1985 | Tateosian .................. 523/212 |

FOREIGN PATENT DOCUMENTS 2411535 9/1974 Fed. Rep. of Germany .
2094326 9/1982 United Kingdom .

OTHER PUBLICATIONS

Chemical Abstracts, vol. 78, No. 20, May 21, 1973, p. 265, Ref. No. 128400h; Columbus, Ohio (Stanley et al.).

*Primary Examiner*—John C. Bleutge
*Assistant Examiner*—Arthur H. Koeckert
*Attorney, Agent, or Firm*—Edward J. Hanson, Jr.; David E. Wheeler

[57] ABSTRACT

Biocompatible, shelf-stable, polymerizable compositions which are especially useful for applications requiring direct contact with living pulpal tissue, bone or dentin, and methods for using the compositions are disclosed. The compositions are non-toxic, both before and after in situ polymerization, and include at least one polymerizable monomer or prepolymer which polymerized by a mechanism other than chelation or saponification. In one aspect, the compositions comprise at least one non-toxic polymerizable ethylenically unsaturated monomer or prepolymer and a catalytically effective amount of a free radical initiator system, and preferably, from about 5 to about 70% by weight of calcium hydroxide or calcium oxide.

24 Claims, No Drawings

METHOD OF TREATING LIVING PULP TISSUE

This is a division of application Ser. No. 696,193, filed Jan. 29, 1985.

BACKGROUND OF THE INVENTION

This invention relates to biocompatible compositions and, more particularly, to compositions which are polymerizable or curable to form products which may be polymerized in situ in contact with living animal tissue, especially dentin, bone and living pulpal tissue, and which are particularly well suited for use as dental cavity liners, in pulp capping and pulpotomy, as endodontic and other dental filling materials, and as cements.

It has long been known that calcium hydroxide may serve as a protective barrier for pulpal tissue against the attack of acid from certain filling materials by acting as a neutralizing agent for the acids in cements and toxic elements eluted from filling materials. It also has been known for some time that calcium hydroxide has a stimulating effect on the formation of secondary dentin when the calcium hydroxide is applied near or on actual exposures of living pulp. This stimulation often is important as an adjunct to successful therapeutic treatment.

In the past, in order to place calcium hydroxide, or a calcium hydroxide former, such as calcium oxide, adjacent an exposed surface of living dentin or pulpal tissue, the calcium hydroxide was dispersed in water, or in an aqueous or organic solution of a film former, and brushed or otherwise applied over prepared surfaces of tooth cavities. These prior art aqueous dispersons apparently were innocuous and non-toxic to pulpal tissue and their use was reasonably successful. However, the use of aqueous dispersons which contain film formers was deficient in that a relatively long time was required for volatilization of the water and the resultant formation of the films. By contrast, the use of organic solvent systems, such as those systems comprised of calcium hydroxide, a film former and chloroform, required considerably less time for solvent evaporation and film formation. However, the use of such organic solvent systems posed problems because of the toxic effects of the solvents on pulpal tissue. Thus, although film formation was rapid, the use of organic solvents limited the application of organic solvent systems to instances where no involvement between the solvent and pulpal tissue was anticipated.

As one means of overcoming the deficiencies of some of the earlier aqueous and organic solvent systems, attempts were made to combine calcium hydroxide in certain systems that were usable as self-hardening pastes. One such self-hardening system is disclosed in U.S. Pat. No. 3,047,408 to Dougherty. In that patent there is described a dental composition comprised of a stoichiometric excess of calcium hydroxide mixed with an ester of a polyhydric alcohol and salicylic acid or its esters. The mixture reacts to form a rigid and permeable mass of calcium phenolate having available calcium hydroxide dispersed therein. Another system of this general type is disclosed in U.S. Pat. No. 4,240,832 to Jandourek. The Jandourek system comprises two pastes and is based upon calcium hydroxide and a condensate of an ester of salicylic acid and an aldehyde, such as formaldehyde or its oligomers.

For the most part, hardenable systems of the type disclosed in the Dougherty and Jandourek patents offer advantages over the earlier calcium hydroxide containing systems, and have been useful as dental cavity liners and pulp capping materials. However, under leaking fillings, the hardenable systems based on esters of salicylic acid tend to undergo hydrolysis which eventually may allow bacterial invasion, infection and secondary caries. These systems also exhibit relatively low compressive strengths, e.g., on the order of about 1500 to about 4000 psi, and relatively high water and acid solubility. Accordingly, when used as a cavity liner, a relatively thick layer of the material must be used so as not to crack under the pressures associated with the plugging of a dental filling material, for example, a dental alloy, onto the liner.

It also has been disclosed in UK Patent Application No. 2094326A to provide a restorative dental material including calcium hydroxide, a bisphenol-A glycidyl methacrylate prepolymer and a polymerization catalyst such as an organic peroxide and an amine. The materials disclosed in this UK application are self-hardenable compositions which must be stored in multiple packages until they are mixed and placed in a tooth preparation by a dentist.

SUMMARY OF THE INVENTION

It is an object of the present invention to provide an improved polymerizable composition which is suitable for use as a cavity liner, in pulp capping and pulpotomy, and as endodontic or other dental filling materials, or as a cement.

It is another object to provide a composition which contains calcium hydroxide, which is substantially resistant to hydrolysis and which exhibits low water solubility, high acid resistance, and sufficient compressive strength so as not to fail when subjected to the pressures associated with the plugging of a dental filling material thereon or with mastication.

Yet another object is to provide a biocompatible dental composition which can be used in direct contact with living pulpal tissue.

Still another object is to provide a hardenable, calcium hydroxide containing polymerizable monomer or prepolymer composition which is non-toxic to living pulpal tissue, which can be cured in situ by free radical reaction, and which, when cured, will not fail when subjected to the pressures of mastication or dental plugging, even when applied as a relatively thin layer.

Another object is to provide a non-toxic composition which is curable by free radical reaction, rigid after cure, flowable before cure, biologically acceptable to dentin, bone and pulpal tissue, highly resistant to inorganic acids, such as phosphoric acid, and substantially insoluble in water when cured.

Yet another object is to provide a free radical curable, calcium hydroxide containing dental composition which is radiopaque and suitable for use in direct contact with dental pulp and/or dentin.

Another object is to provide a visible light curable, calcium hydroxide containing dental composition, which is non-toxic to dentin and living pulpal tissue and which can be stored as a shelf-stable one paste system prior to cure.

Yet another object is to provide an improved dental composition which is suitable for use as a functional composite or as a pit and fissure sealant.

Still another object is to provide a biocompatible composition which is polymerizable in situ in contact with living animal tissue, especially mammalian tissue.

DETAILED DESCRIPTION

The above and other objects and advantages are accomplished in one aspect, by providing a polymerizable mixture comprising a monomer or prepolymer material having terminal carbon-to-carbon unsaturation, e.g., an ethylenically unsaturated monomer, dimer, trimer, oligomer, or adduct, and a free radical initiator system for effecting in situ polymerization of the mixture. In a preferred aspect of the invention, the polymerizable mixture also comprises calcium hydroxide or a calcium hydroxide forming material such as calcium oxide, and optionally another filler.

Essential features of the polymerizable composition of the invention are that the monomer or prepolymer components thereof are substantially non-toxic to living pulpal tissue, dentin or bone, that the overall composition is substantially non-toxic to living pulpal tissue, dentin or bone prior to polymerization or cure, and that the composition can be polymerized in situ to a hardened mass that is substantially non-toxic to living pulpal tissue, dentin or bone.

In other aspects of the invention, the polymerizable composition also contains a radiopaque filler such as barium sulfate, and the initiator system is one which is operable upon exposure to visible light Some of the polymerizable monomer or prepolymer materials which may be used in preparing the polymerizable mixtures of the present invention may not be novel in and of themselves. However, the use of such monomer or prepolymer materials to form in situ polymerizable compositions which are non-toxic toward living pulpal tissue or bone, and therefore usable in direct contact with living pulpal tissue or bone, has not been disclosed in the prior art.

Thus, the polymerizable monomer or prepolymer materials which are contemplated for use in the present invention are those monomer or prepolymer materials which polymerize by a mechanism other than by chelation or saponification, and which result in the formation of preferred polymerized or cured compositions which are substantially resistant to hydrolysis, which exhibit high acid resistance and low water solubility, and which are characterized by sufficient compressive strength so as not to fail when subjected to the stresses associated with the plugging of a dental filling material thereon or with mastication. Another feature of the suitable monomer or prepolymer materials is that they are biocompatible, i.e. observably non-toxic to living mammalian tissue, especially iving pulpal tissue, dentin or bone, both when in the uncured monomeric or prepolymeric state, while being cured, and after being cured in situ in contact with living mammalian tissue.

One accepted method for determining the necessary biocompatibility of various compositions toward living tissue is an in vitro cell culture biocompatibility method wherein samples of the compositions to be tested are extracted in a bovine serum solution in a Minimum Essential Medium (MEM), whereafter the bovine serum solution and specified animal cells, such as human (WI-38), L929 mouse fibroblast cells or their equivalent, are incubated in a MEM for a predetermined period of time, and the incubated cells are visually observed and graded for cytotoxic manifestations. See, for example, R. E. Wilsnack, *Quantitative Cell Culture Biocompatibility Testing of Medical Devices and Correlation To Animal Tests*, Biomat, Med. Dev. Art. Org., 4(3& 4), 235–261 (1976). In connection with the present compositions, the in vitro cell culture method preferably is performed using L929 mouse fibroblast cells which have been cultured in a growth medium consisting of 5% bovine serum solution in MEM, wherein the bovine serum solution initially was used to extract a specified mass of cured or uncured material, as the case may be, and wherein the cells were incubated at 37°±2° C. for a specified period of time, e.g., 24, 48 or 72 hours. The degree of toxicity may be stated as a function of the percentage of the cells which have been lysed or fixed over the test period. For the purposes of this patent application, the observable cytotoxic manifestations may be graded qualitatively as follows: non-toxic, no cell lysis or fixation; slight intermediate response, up to 10% cell lysis; intermediate response, between 10% and 50% cell lysis or fixation; and, toxic response, greater than 50% cell lysis or fixation.

In general, lysed cells are dead cells that have ruptured cell walls. Fixed cells are cells that are dead and are attached to the walls of the flask and may be lysed. Fixation normally occurs at a high percentage of cells lysed and is considered a severe response.

Another accepted method for determining the necessary biocompatibility of the various compositions toward living tissue, particularly living pulpal tissue and dentin, is an in vivo test which involves filling prepared teeth of a primate, such as *Cynomolgus Fascicularis*, with a filling composition to be tested, sacrificing the animal after a predetermined period of time, excising the filled teeth and subjecting them to routine histological evaluation. The excised teeth are observed for evidence of chemical mummification and are graded subjectively on a scale from 0 to 4 for pulpal response. A grade of zero represents no inflammation; 1, mild response; 2, moderate irritation; 3, severe inflammation; and 4, abscess formation or pulp necrosis. See, for example, H. R. Stanley et al, *Compatibility of Various Materials with Oral Tissues II: Pulp Responses to Composite Ingredients*, J. Dent. Res., 58(5), pp 1507–1517 (May 1979).

For the purpose of this invention, a polymerizable monomer or prepolymer material or a polymerizable composition containing such monomer or prepolymer material and, for example, a filler, is suitable for use only if there is observed less than 10% cell lysis, and preferably no lysis or fixation after an incubation period of 72 ±4 hours when tested in accordance with the above in vitro cell culture biocompatibility method, or if it receives a grade of 1 or less, and preferably zero in the above in vivo primate test. The preferred primate to be used for this latter test is *Cynomolgus Fascicularis*.

In one aspect of the invention, the monomer or prepolymer material comprises at least one polymerizable ethylenically unsaturated material, and the polymerizable composition containing the monomer or prepolymer material also contains a free radical initiator system. Among the suitable monomer or prepolymer materials which contain ethylenic unsaturation there may be mentioned the vinyl urethane or urethane acrylate or urethane methacrylate materials which are well known in the art. These materials are polymerizable by free radical initiation and may comprise the reaction product of an organic diisocyanate or an isocyanate-terminated urethane prepolymer and an ethylenically unsaturated monomer containing groups reactive with the diisocyanate or diisocyanate prepolymer. The urethane prepolymers, which may be linear or branched, carry isocyanate groups and generally are prepared by reacting a compound having hydroxyl functionality with a molar excess of diisocyanate. Alternatively, the vinyl urethane or urethane acrylate or urethane methacrylate materials may be prepared by reacting suitable hydroxyl-containing prepolymers with isocyanto-containing acrylates and methacrylates.

Any of a wide variety of isocyanates may be used to prepare the isocyanate-terminated urethane prepolymer including aliphatic, cycloaliphatic, heterocyclic, and aromatic isocyanates, and combinations of these. Examples include, but are not limited to 2,4-tolylene diisocyanate, 2,6-tolylene diisocyanate, 1,4-phenylene diisocyanate, hexamethylene diisocyanate, 1,4-naphthalene diisocyanate, 4,4'-diphenyl diisocyanate, butylene-1,4-diisocyanate, ethylene diisocyanate, trimethylene diisocyanate, tetramethylene-1,4-diisocyanate, butylene-2,3-diisocyanate, cyclohexylene-1,2-diisocyanate, methylene-bis-(4-phenyl isocyanate), methylene-bis-(4-cyclohexyl isocyanate), diphenyl-3,3'-dimethyl-4,4'-diisocyanate, xylylene diisocyanate, cyclohexane-1,4-diisocyanate, 1-methoxyphenyl-2, 4-diisocyanate and the like, and mixtures thereof.

A wide variety of compounds having hydroxyl functionality may be used to form the isocyanate-terminated urethane prepolymers. For example, suitable hydroxyl containing compounds include diols and polyols such as ethylene glycol, propylene glycol, triethylene glycol, tetramethylene glycol, polyethylene glycol, trimethylolpropane, pentaerylthritol, dipentaerythritol, and the like, or esters of acrylic acid, methacrylic acid or itaconic acid or the like with aliphatic polyhydric alcohols. Suitable ethylenically unsaturated hydroxyl containing compounds are the esters of acrylic or methacrylic acid, hereinafter referred to as (meth)acrylic acid or (meth)acrylate esters, and a hydroxyalkanol of at least two carbon atoms such as hydroxyethyl(meth)acrylate, hydroxypropyl (meth)acrylate, hydroxyisopropyl (meth)acrylate, and the like.

Formation of the isocyanate-terminated urethane prepolymers and vinyl urethanes may be assisted by the use of catalysts known in the art assist polyurethane formation, for example, tetiary amines and metal salts, e.g., stannous octoate. It is important however, to utilize a catalyst which results in the ultimate composition, both cured and uncured, having no more than 10% observable cell lysis toward the selected cells, e.g., L929 mouse fibroblast cells, which have been cultured in 5% bovine serum solution in a MEM as outlined above and as illustrated more fully in the examples hereinafter. One catalyst that generally is to be avoided is dibutyl tin dilaurate.

Vinyl urethanes are well known in the art and are described for example, in U.S. Pat. Nos. 3,629,187 to Waller, 3,759,809 to Carlick et al, 3,709,866 to Waller and 4,459,193 to Ratcliffe et al, all of these patents being incorporated herein by reference. Not all of these known vinyl urethanes are suitable for use in the present invention, however, at least in part because the catalyst systems used in their preparation have rendered them toxic to living mammalion tissue.

In a preferred aspect of the invention, the vinyl urethane or urethane-(meth)acrylate monomer or prepolymer materials are characterized by the structural formula

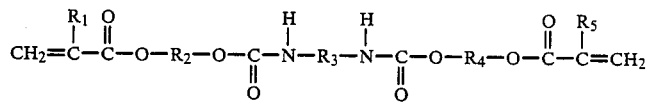

wherein $R_1$ and $R_5$, independently, are H, alkyl or substituted alkyl; $R_2$ and $R_4$, independently, are alkylene, subs tuted alkylene, cycloalkylene, substituted cycloalkylene, arylene or substituted arylene; and, $R_3$ is alkylene, substituted alkylene, cycloalkylene, substituted cycloalkylene, arylene, substituted arylene, heterocyclic, substituted heterocyclic, the reaction product of an organic diisocyanate or an isocyanate terminated prepolymer and a compound having hydroxyl functionality, or the reaction product of a polyol or a hydroxyl terminated prepolymer and a compound having isocyanto functionality.

In a more preferred embodiment, $R_1$ and $R_5$, independently, are H or $C_1$-$C_4$ alkyl; $R_2$ and $R_4$, independently, are $C_1$-$C_6$ alkylene; and $R_3$ is $C_1$-$C_6$ alkylene, $C_2$-$C_{12}$ substituted alkylene, the reaction product of an organic diisocyanate or polyisocyanate with an alkanol or polyalkanol. In a still more preferred embodiment, $R_1$ and $R_5$, are H or —$CH_3$; $R_2$ and $R_4$ are

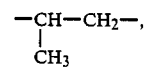

—$CH_2$—$CH_2$—$CH_2$—, or —$CH_2$—$CH_2$—; and $R_3$ is

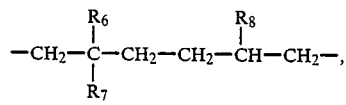

where $R_6$, $R_7$ and $R_8$, independently, are H or —$CH_3$.

Of course, the foregoing examples of polymerizable ethylenically unsaturated monomers and prepolymers are intended to be exemplary only, and other known polymerizable materials which satisfy the criteria outlined above can be used in the compositions of this invention.

The polymerizable materials exemplified above can be employed alone or in any mixture thereof. Among the above-mentioned polymerizable materials, mixtures of the urethane-(meth)acrylate and polyfunctional (meth)acrylates generally are preferred.

As initiator systems that may be employed in the present invention there may be mentioned those systems of the room temperature cure type. Among such systems, there may be mentioned the known amine-peroxide and amine-peroxide-sulfinic acid salt types. Photoinitiator systems also may be used and these are used in preferred embodiments since they may be used to formulate curable compositions in a one package system.

Suitable photoinitiators for the compositions of this invention include, but are not limited to the following: acyloins, acyloin derivatives, such as benzoin methyl ether, benzoin ethyl ether, desyl bromide, desyl chloride, desyl amine, and the like, ketones, such as benzophenone, acetophenone, cyclopentadione, benzil, caprone, benzoin cyclobutadione, and the like, substituted benzophenones, such as N,N'-dimethylamino benzophenone, Michler's Ketone, and halogenated aceto- and benzophenones; polynuclear quinones, such as benzoquinone and anthraquinone; substituted polynuclear quinones, such as chloranthraquinone, chloronaphthoquinone, dichloronaphthoquinone, and so forth. These systems generally also employ a small amount of an accelerating agent, such as the amines, mercaptans and their derivatives, amine oxides or the like.

In the preferred embodiment of the invention, the initiator system that is employed is one that is operative upon exposure to visible light, or near visible light, particularly that having a wavelength in the range of from about 360 to 550 nm (nanometer). The radiation may be generated by conventional lamps, e.g., quartz halogen, and may conveniently be directed onto the composition using fibre optics. One such system would comprise an α-diketone photosensitizer and an organic nitrogen compound, such as an amine, which is capable of reducing the photosensitizer when the photosensitizer is in the excited state. A suitable α-diketone photosensitizer which is readily available is camphoroquinone, and a suitable amine reducing agent is methyl diethanol amine. Other suitable α-diketone photosensitizers and other suitable amine reducing agents for the photosensitizers are disclosed, for example, in U.S. Pat. Nos. 4,457,818 to Denyer et al, 4,089,763 to Dart et al and 4,071,424 to Dart et al, these patents being incorporated herein by reference.

The amount of initiator system to be used depends largely upon its identity. When a visible light curing system is used, the amount of α-diketone to be used generally is from about 0.001 to about 10%, preferably from about 0.01 to about 5%, based on the polymerizable monomer or prepolymer in the composition, and the amount of amine reducing agent is from about 0.1 to about 5%, by weight based on the polymerizable monomer or prepolymer in the composition. Using amounts of α-diketone and amine in these ranges enables the compositions to be cured into hard, strong solids in from about 5 to about 40 seconds.

In yet another preferred aspect of the invention, the polymerizable compositions also include calcium hydroxide or a calcium hydroxide former, such as calcium oxide. In this aspect, the compositions of the present invention are particularly well suited for dental applications since they stimulate the formation of secondary dentin when they are polymerized in situ near or on actual exposures of living pulpal tissue.

The calcium hydroxide or calcium hydroxide former should be added to the compositions in the form of a fine powder, and should be present in an amount of from about 1 to about 99, preferably from about 3 to about 70%, and more preferably from about 5 to about 30% based on the weight of the composition.

The compositions also may include a sufficient amount of a powdered substance which is opaque to X-rays and which is inert to the calcium hydroxide and other components of the compositions so as to render th cured compositions radiopaque. One suitable X-ray opaque substance is barium sulfate, but any other compatible radiopaque substance such as barium or strontium oxide glasses may be used. Generally speaking, when a radiopaque filler is used in addition to calcium hydroxide or a calcium hydroxide former, the radiopaque filler may be added in amounts up to about 99% by weight of the composition, with amounts ranging from about 3 to about 70% weight being preferred, and amounts ranging from about 5 to about 30% by weight being more preferred. Normally, it is preferred that the percentage by weight of calcium hydroxide to the percentage by weight of radiopaque filler be in the range of from about 30–70% to 70–30%. In practice, excellent results are attained when approximately equal parts by weight of each substance is used, particularly when the calcium hydroxide and radiopaque filler are treated with a silane coupling agent such as gamma-methacryloxypropyltrimethoxy silane, gamma-aminopropyltriethoxysilane and gamma-glycidoxypropyltrimethoxysilane.

The compositions also may include other fillers, such as colloidal silica, fused quartz, aluminum oxide, ceramic and/or glass beads, calcium phosphates, especially calcium apatite, metal silicates and aluminosilicates and the like, either singly or in admixture, in place of or in addition to the radiopaque filler, and further may include small quantities of other materials such as anti-oxidants and stabilizers provided that they do not substantially effect cure and, more importantly, toxicity. The total amount of filler in the copositions may be as high as about 99% by weight, preferably as high as about 85% by weight, and more preferably as high as about 60% by weight. In one aspect, the above fillers may be used in amounts ranging from about 45 to about 90% by weight. It is preferred that the filler, including the calcium hydroxide or calcium hydroxide former, be in the form of particles having an average diameter on the order of from about 0.02 to about 20 $\mu$.

The amount of polymerizable monomer or prepolymer material used in the compositions of the invention may vary over relatively wide limits depending, at least in part, upon the intended use Generally speaking, however, the polymerizable monomer or prepolymer is present in amount ranging from about 1 to about 99.8%, and preferably from about 15 to about 95% by weight of the composition. Most preferably the polymerizable monomer or prepolymer is present in amounts ranging from about 40 to about 70% by weight. In many preferred aspects of the invention, the polymerizable monomer or prepolymer is present in an amount of at least about 30% by weight.

Mixing of the components of the present invention may be accomplished by a variety of known techniques. For example, the powder components of the composition may be blended separately from the liquid components and the separate powder and liquid blends may be mixed at the time of use. Such separate blends may be provided in the form of a kit composed of one or more powder components and one or more liquid components which may be mixed by a dentist when needed. In an alternative procedure, the components, both powder and liquid, may be blended prior to shipment and, depending upon the nature of the initiator system, may be packaged as single package or multiple package systems.

In one embodiment, the compositions may be prepared by first mixing the calcium hydroxide and radiopaque or other filler components, preferably together with a silane coupling agent, and then mixing the blended calcium hydroxide and radiopaque fillers together with the polymerizable components. When a room temperature active initiator system of the peroxide-amine type, for example, is used, the peroxide and amine portions thereof must be kept separate until immediately prior to use. Accordingly, the compositions of this invention which use this type of initiator system must be kept separate until immediately prior to use. Accordingly, the compositions of this invention which use this type of initiator system must be prepared as multiple package systems wherein the amine may be mixed with a first portion of the polymerizable components and filler in a first package, and the peroxide may be mixed with a second portion of the filler and polymerizable components in a second package. While two package systems have been used with success in dentistry, it is preferable to use single package systems to avoid the need for accurately measuring the various components required to be dispensed from more than one package at the time of use. The use of a one package system also eliminates the need for mixing the various components at the time of use, thus avoiding the possibility of including air bubbles in the compositions, which air bubbles tend to inhibit the rate of cure and weaken the cured structure.

When a photosensitive initiator system is used which permits all of the components of the composition to be blended into a shelf stable, one package system, such as when an α-diketone and an amine are used, the silanated, blended calcium hydroxide and radiopaque or other filler is mixed together with the polymerizable components including the initiator system, stabilizers, etc. This mixing may be accomplished, for example, in a three-roll mill, ball mill, high shear disperser, or the like, in accordance with known dispersion techniques. However, the polymerizable monomer or prepolymer, optionally together with copolymerizable monomers, conveniently may be diluted with a suitable non-reactive or reactive diluent so as to reduce the viscosity, thus enabling adequate mixing of the fillers to be achieved more readily and to make the composition a more flowable material for desired clinical handling characteristics. When mixing has been effected with the use of a non-reactive diluent, the diluent should be removed e.g., by evaporation.

When a photosensitive initiator system is used that renders the composition sensitive to light in the 360 to 550 nm visible or near visible range, that part of the preparation of the present composition in which photosensitive catalyst is added should be carried out in the substantial absence of light in that range. Most conveniently the preparation can be carried out using light outside that range, for example, under light emitted by sodium vapor electric discharge lamps. In this manner, shelf-stable single package compositions can be prepared.

In order to further protect the present compositions from partial curing in daylight, in one preferred embodiment it is envisaged that the compositions can be dispensed from containers which are opaque to actinic light.

The compositions of the present invention are gel-free fluid systems at ambient temperatures, and the viscosity and consistency of the compositions may be controlled by adjusting the mixture of the polymerizable components, calcium hydroxide and/or fillers.

Light free ambient self stability is an important atribute of the preferred embodiment of the present invention. It is particularly a problem to attain shelf stability with single package calcium hydroxide containing composition of the type of the present invention. This usefulness of the preferred composition of the present invention is not destroyed under accelerated aging test when the composition is heated at 50° C. for 7 days.

The compositions of the present invention may be applied to a prepared bone or tooth surface, including living pulpal tissue, by any suitable means generally known in the art, and then cured by exposure to appropriate radiation.

As used herein the term "monomer or prepolymer" is meant to define any monomer, dimer, trimer, oligomer or adduct or prepolymer which can be polymerized into a hardened mass.

While there are disclosed below but a limited number of embodiments of the invention herein presented, it is possible to practice still other embodiments without departing from the inventive concept herein disclosed. It is desired therefore, that only such limitations be imposed on the appended claims as are stated therein. Unless otherwise specified, all parts are given by weight.

EXAMPLE 1

An adduct of hydroxypropyl methacrylate (HPMA) (Rocryl 410, a product of Rohm & Hass Co.) and trimethyl hexamethylene diisocyanate (TMDI) (a product of Veba Chemic AG) was prepared by reacting 40.76 g. of TMDI with 59.19 g. of HPMA in the presence of 0.05 g. stannous octoate (Catalyst T-9, a product of M & T Chemical, Inc.).

A silanated filler was prepared in a tumble mixer by charging the following ingredients to the mixer while the mixing operation continued. 50 parts by weight of $Ca(OH)_2$, 50 parts by weight $BaSO_4$, and 1 part by weight of silane γ-methacryloxypropyltrimethoxy silane, Silane A-174, a product of Union Carbide Corp.) with 100 parts by weight of ½ inch Borundum cubes. The tumbling was continued for 2 hours, whereafter the Borundum cubes were separated from the silanated filler by sieving through a number 10 screen. Approximately 37.72 g. of the silanated filler was yielded.

The HPMA was prepared for reaction with the TMDI by drying the HPMA with molecular sieves to less than 300 PPM water and charged into a dry, clean reactor. 300 PPM of the methyl ether of hydoquinone (MEHQ) based on the weight of the HPMA was then charged into the reactor. Then 0.05 g. of stannous octoate was charged into the reactor. The reactor was then equipped with a mixing shaft, thermometer, separatory funnel for the TMDI addition, and an adapter with an air inlet tube extending down under the HPMA surface with a reflux condenser on top of the adapter. The top outlet of the condenser was connected with a drying tube containing anhydrous magnesium sulfate. The reactor was purged with dry air and purging was maintained constantly through all the reaction time. The HPMA was heated in the reactor to about 50° C.±3° C. under constant mixing and dry air purging.

Then began the charging of 40.76 g. of the TMDI into the dry separatory funnel. The TMDI was charged into the reactor at a rate that maintained the temperature of the reaction at 50° C.±3° C. When the temperature increased, heat was removed and a cooling water bath was used to adjust the temperature. After completion of the TMDI addition, the mixture was maintained at about 50° C.±5° C. for about 16 hours with constant mixing and dry air purging. Then the heat was turned up and the temperature raised to about 70° C. ±2° C., with constant mixing and dry air purging. Mixing was continued for about 8 more hours.

A sample taken for % NCO analysis showed less than 0.01% residual NCO. The product was then discharged at 70° C., and a sample was taken for viscosity testing. A viscosity of about 18,000 cps at 25° C. was noted.

56.57 g. of the HPMA-TMDI adduct prepared above was charged to a Ross mixer pot and the following materials were then added in the order given while the mixer was in operation and mixing was continued for 30 minutes. 5 g. of triethylene glycol dimethacrylate (TEGDMA), 0.311 g. of butylated hydroxy toluene (BHT), 0.311 g. of methyldiethanol amine (MDEA) and 0.092 g. of camphoroquinone (CQ.).

Next, one half of the silanated filler previously prepared was charged to the Ross mixing pot and mixed until wet. Then the remaining filler was added and the components were mixed thoroughly until wet. The mix was then scraped from the sides of the pot and the mixer blades and then mixing was undertaken for an additional 10 minutes. After this the mix was removed from the pot and rolled through a three roll mill to complete the formation of a shelf-stable, uncured, calcium hydroxide containing polymerizable composition that can be cured by exposure to visible light, for example, from a Prisma-Lite® light curing unit (sold by L. D. Caulk Division of Dentsply International, Inc.) for a period of from about 5 to about 40 seconds to yield a hardened mass having a compressive strength on the order of about 12,000 to 15,000 psi.

EXAMPLE 2

Example 1 was repeated except that 0.05 g. of dibutyl tin dilaurate was substituted for the stannous octoate.

EXAMPLE 3

Example 1 was repeated except the 1.0 g. of dibutyl tin dilaurate (DBTDL) was substituted for the stannous octoate.

EXAMPLE 4

Example 1 was repeated except that the HPMA-TMDI adduct was replaced by 56.57 g. of a 50:50 mixture of triethylene glycol dimethacrylate (TEGDMA) and the reaction product of 1.08 equivalents of bis-phenol-A glycidyl methacrylate (Bis-GMA) and 1.00 equivalents of hexamethylene diisocyanate (HMDI). The composition of this example when exposed to visible light from a Prisma-Lite® light curing unit for about 10-30 seconds and on testing (as set forth in Example 6) was found to be toxic and generally not within the scope of this invention. The test results are shown in Table I.

EXAMPLE 5

Example 1 was repeated except that the HPMA-TMDI adduct was replaced by an equal amount of Bis-GMA. The composition of this example was tested as set forth in Example 6, and the test results are shown in Table 1.

EXAMPLE 6

Samples of the curable calcium hydroxide containing compositions of Examples 1-5 were tested for cytotoxicity both in the cured and uncured state. A sample of calcium hydroxide powder also was tested. The tests were made by a tissue culture method utilizing monolayers of strain L929 mouse fibroblast cells in a growth medium consisting of 5% bovine serum solution in a Minimum Essential Medium (MEM). For each test, a specified mass of cured or uncured calcium hydroxide containing composition (sample) was extracted with 10 ml of a 5% bovine serum solution in MEM for 24 hrs. at 37°±2° C. A negative control for each sample tested was made by using a similar 10 ml. 5% bovine serum that was heated for 24 hrs. at 37°±2° C. without contact with the sample. A positive control also was made in which 10 ml. of a 5% bovine serum solution in MEM was used to extract 0.47 g. of black rubber for 24 hrs. at volume of the sample MEM extract to a monolayer of L929 mouse fibroblast cells, while adding 5 ml. volumes of the negative control solution and the positive control solution to separate monolayers of L929 mouse fibroblast cells. The cells were then incubated at 37°±2° C. for 72 ±4 hours. Cells were observed at 24, 48 and 72 hours for cytotoxic manifestations.

The results of the tests are set forth in Table I.

TABLE I

| | Tissue Culture MEM Elution Test Results | | | | |
|---|---|---|---|---|---|
| Material Tested (Example No.) | Quantity Tested (Mg) | Curing Time (Seconds) | 24 hr* results (% Lysed or fixed) | 48 hr. results (% Lysed or fixed) | 72 hr** results (% Lysed or fixed) |
| 1 | 35 | 10 | 0 | 0 | 0 |
| 1 | 35 | 20 | 0 | 0 | 0 |
| 1 | 35 | 30 | 0 | 0 | 0 |
| 2 | 5 | 10 | 0 | 0 | 0 |
| 2 | 5 | 20 | 20 | 70 | — |
| 2 | 5 | 30 | 100 | — | — |
| 2 | 35 | 10 | 10–15 | 60 | — |
| 2 | 35 | 20 | >80 | — | — |
| 2 | 35 | 30 | 90 | — | — |
| 2 | 50 | 10 | 50–60 | — | — |
| 2 | 50 | 20 | 50–60 | — | — |
| 2 | 50 | 30 | 90 | — | — |
| 3 | 5 | 10 | 10–15 | 10–15 | 10–15 |
| 3 | 5 | 20 | 0 | 0 | 0 |
| 3 | 5 | 30 | 0 | 0 | 0 |
| 3 | 35 | 10 | 100 | — | — |
| 3 | 35 | 20 | 0$^b$ | 70–80 | — |
| 3 | 35 | 30 | 80 | — | — |
| 3 | 50 | 10 | 100 | — | — |
| 3 | 50 | 20 | 100 | — | — |
| 3 | 50 | 30 | 100 | — | — |
| 4 | 35 | 10 | 100$^a$ | — | — |
| 4 | 35 | 20 | 20–30 | 40 | 40–50 |

TABLE I-continued

Tissue Culture MEM Elution Test Results

| Material Tested (Example No.) | Quantity Tested (Mg) | Curing Time (Seconds) | 24 hr* results (% Lysed or fixed) | 48 hr. results (% Lysed or fixed) | 72 hr** results (% Lysed or fixed) |
|---|---|---|---|---|---|
| 4 | 35 | 30 | 0 | $0^b$ | $0^b$ |
| 5 | 35 | 10 | 0 | 10–15 | 20–25 |
| 5 | 35 | 20 | 0 | $0^b$ | $0^b$ |
| 5 | 35 | 30 | 0 | $0^b$ | $0^b$ |
| 1; uncured | 35 | 0 | 0 | $0^b$ | $0^b$ |
| 1; HPMA-TMDI adduct only; uncured | 20 | 0 | 0 | 0 | 0 |
| | 15 | 0 | 0 | 0 | 0 |
| 2; HPMA-TMDI Adduct only; uncured | 29 | 0 | $100^a$ | — | — |
| | 20 | 0 | $100^a$ | — | — |
| | 3 | 0 | $100^a$ | — | — |
| 3; HPMA-TMDI Adduct only; uncured | 25 | 0 | 100 | — | — |
| | 2 | 0 | 100 | — | — |
| Calcium Hydroxide | 25 | 0 | 100*** | — | — |

*Positive Control - toxic (>50% Lysis) in 24 hours for each test.
**Negative Control - nontoxic (no Lysis) in 72 hours for each test.
***All cells dead after 2 hours after extract placed on cells.
$^a$Severe reaction, cells fixed.
$^b$Swelling of cells noted, no lysis. Slight intermediate response.

The results of Table I indicate that compositions in which dibutyl tin dilaurate was used as the catalyst were generally toxic after 24 hours, when cured, when samples over 5 mg. were tested. Uncured adduct, prepared using (DBTDL) was toxic after 24 hours, when samples as small as 2 mg. were tested. Accordingly, these compositions do not fall within the scope of the present invention.

The following procedure ws carried out to further confirm the toxicity, non-toxicity parameters of the invention.

EXAMPLE 7

A filler-free polymerizable composition was prepared by charging 33.11 parts of methylene-bis-(4-cyclohexyl isocyanate) (MBCI) into a reactor which has been dried and purged with dry air. Then 0.05 parts by weight of stannous octoate (S.O.743) and 41.07 parts of polytetramethylene ether glycol (Teracol 650, a product of E. I. du Pont Company), were added to the reactor. The Teracol 650, which was dried to a water content of less than about 200 PPM, was charged to the reactor by means of a separatory funnel under thorough mixing and constant dry air purging. The temperature in the reactor tended to rise gradually due to the exothermic reaction between the MBCI and Teracol 650, and was maintained at about 50° C.±3° C. during the addition of the glycol (Teracol 650) by means of a cooling water bath. After completion of the addition of the glycol, the mixture was heated and the temperature raised to about 75° C.±5° C. The mixture was maintained at this temperature with constant mixing and dry air purging for about 3 hours.

Then began the gradual charging of 25.78 parts of hydroxypropyl methacrylate (HPMA) into the reactor, while the mixture was maintained at about 80° C.±5° C. with constant mixing and dry air purging for about 3 hours.

A sample taken for % NCO analysis indicated that the residual NCO content was less than 0.01%.

The polymerizable adduct prepared above was subjected to the tissue culture MEM test in accordance with the procedure outlined in Example 6 and the results of the test are shown in Table II. Due to a procedural error, initial test results (Run 1) were defective and the test was repeated (Run 2).

EXAMPLE 8

The procedure of Example 7 was repeated, except that the reaction product, before being subjected to the tissue culture MEM test, was charged to a Ross mixer pot and 0.311 parts of BHT, 0.311 parts of MDEA and 0.092 parts of C.Q. were added in the order given while the mixer was in operation and mixing was continued for 30 minutes. The composition of this example was cured when exposed to visible light for about 1–30 seconds and on testing for toxicity in accordance with the procedure with the procedure of Example 6 was found to be non-toxic. The results of the testing is shown in Table II.

EXAMPLE 9

The procedure of Example 7 was repeated, except that 1 part of dibutyl tin dilaurate (DBTDL) was used in place of the S.O. The results of the tissue culture MEM test are shown in Table II.

EXAMPLE 9A

The procedure of Example 8 was repeated, except that 1 part of dibutyl tin dilaurate (DBTDL) was used in place of the S.O. The results of the tissue culture MEM test are shown in Table II.

EXAMPLES 10–15

A polymerizable dental composite was prepared by mixing 20 parts of the polymerizable HPMA-TMDI adduct of Example 1 with 80 parts of Raysorb T3000 (barium alumino silicate glass). The resulting composite materials, both cured (Example 11) and uncured (Example 10), were found to be non-toxic when tested in accordance with the tissue culture MEM test set forth in Example 6. The results of the tests are shown in Table II. Additional composites were prepared using 30 parts of the polymerizable HMPA-TMDI adduct of Example 1 and 70 parts of Cervit T1000 (lithium alumino silicate glass) (Example 12, uncured and Example 13, cured) and of 28 parts of polymerizable HPMA-TMDI adduct of Example 1 and 72 parts fused quartz (Example 14, uncured; and Example 15, cured). These composite materials also were found to be non-toxic and the tissue culture MEM tests results for these composite materials are shown in Table II.

EXAMPLES 16-18

A two part dental cement was prepared using the polymerizable HPMA-TMDI adduct of Example 1 as the resin-forming binder portion. The "catalyst" portion of the cement (Example 16) comprised the following formulation:

| | |
|---|---|
| HPMA-TMDI | 17.62 parts |
| BHT | .02 parts |
| benzoyl peroxide (BPO) | .44 parts |
| milled Raysorb T3000 | 30.05 parts |
| silica (Aerosil R-972) | 1.15 parts |

The "base" portion of the cement (Example 17) had the following formulation:

| | |
|---|---|
| HPMA-TMDI | 18.42 parts |
| BHT | .003 parts |
| dihydroxyethyl-p-toluidine (DHEPT) | .095 parts |
| milled Raysorb T3000 | 30.05 parts |
| silica (Aerosil R-972) | 1.15 parts |

The admixture of equal parts of "catalyst" and "base" (Example 18) cured to a hardened mass in about 5 minutes. The tissue culture MEM toxity test results (shown in Table II) indicate that the uncured "catalyst", uncured "base" and cured "catalyst" plus "base" were non-toxic.

EXAMPLES 19-21

(Commercially Available Composite Material)

A commercially available dental composite material, sold under the name Adaptic (a product of Johnson & Johnson Dental Products Company) was prepared in accordance with the manufacturer's instructions. The "base" portion of the composite (Example 19) is believed to comprise BIS-GMA, TEGDMA, DHEPT and milled quartz, whereas the "catalyst" portion (Example 20) is believed to comprise BIS-GMA, TEGDMA, BPO and milled quartz. Both the uncured "catalyst" and the uncured "base" were found to be toxic (100 cells lysed) after 48 hours, whereas the cured admixture of equal parts of "base" and "catalyst" (Example 21) was found to exhibit an "intermediate response" (10-50% lysed cells) after 72 hours. The results of the tissue culture MEM tests are shown in Table II.

EXAMPLES 22-24

(Commercially Available Composite Material)

Examples 19-21 were repeated using another commercially available composite material, sold under the name Silar (a product of Dental Products/3M). The uncured "catalyst" (Example 22), the uncured "base" (Example 23) and the cured admixture of equal parts of "base" and "catalyst" (Example 24) all were found to be toxic. The results of the tissue culture MEM tests are shown in Table II.

EXAMPLES 25-26

(Commercially Available Composite Material)

A commercially available one part light cure composite material, sold under the name Silux (a product of Dental Products/3M), was prepared in accordance with the manufacturer's instructions and tested for toxicity in accordance with the procedure outlined in Example 6. Both the uncured material (Example 25) and the cured material (Example 26) were found to be toxic. The toxicity results are shown in Table II.

EXAMPLES 27-28

(Commercially Available Composite Material)

A commercially available composite material, sold under the name Visio-Dispers (a product of Espe Fabrick Pharmazeutischer Preparate GmbH), was prepared according to the manufacturer's instructions and was tested for toxicity in accordance with the procedure of Example 6. The uncured material (Example 27) was found to exhibit a intermediate toxicity response (20% cells lysed) after 72 hours, whereas th cured material (Example 28) was found to be non-toxic after 72 hours. The test results are shown in Table II. The toxicity of the uncured material renders this composite material generally unsuitable for the purposes of this invention.

EXAMPLES 29-31

The silanated fillers used in the composites of Examples 5, 12, and 14 respectively, were tested for cytotoxicity in accordance with the procedure of Example 6. The test results, which are shown in Table II, indicate that the fillers themselves are non-toxic.

EXAMPLES 32-33

A polymerizable composite material was prepared by mixing 20 parts of the polymerizable composition of Example 9 (using DBTDL as the catalyst) and 80 parts of Raysorb T3000. The composite material, which was tested for cytotoxicity in accordance with the procedure of Example 6, was found to be toxic both in the cured (Example 32) and uncured (Example 33) state. The results of the toxicity tests are shown in Table II.

EXAMPLES 34-36

A three part dental restorative material was prepared according to UK patent 2,094,326A. The composition of each part is as follows:

| | |
|---|---|
| Part I powder blend: (Example 34) | |
| Milled, silanated, quartz | 98.60% |
| Benzoyl peroxide (78%) | 1.28% |
| Aerosil 200 (fumed silica) | 0.099% |
| Yellow Iron Oxide | 0.020% |
| Part II powder: | |
| Calcium Hydroxide (U.S.P.) | 100% |
| Part III Liquid Composition: (Example 35) | |
| BIS-GMA | 56.00% |
| HEMA | 15.00% |
| EDMA (ethylene glycol dimethacrylate) | 28.00% |
| Methacrylic acid | 0.50% |
| Methoxy phenol (MEHQ) | 0.06% |
| DHEPT (dihydroxyethyl paratoluidine) | 0.50% |

An equal volume of Part I powder blend and Part II powder blend were mixed with 5 drops of Part III liquid, and the mixture cured to a solid mass. The approximate weight ratio of the above three components was 19:19:62. The cured solid mass (Example 36), the Part I powder blend (Example 34), and the Part III liquid (Example 35) were tested for cytotoxicity in accordance with procedure of Example 6 and, as indicated in Table II, the liquid was found to be toxic after 24 hours, while the Part I powder blend was found to be non-toxic. The cured composition also was found to be non-toxic, although some cell swelling was noted.

adduct of Example 1 were non-toxic after 72 hours, whereas composites made with the DBTDL-catalyst materials of Example 9 showed toxic results (Examples 32–33). The test results of Examples 29–31 show that the glass fillers used in the various composite formulations are themselves non-toxic. The test results of Examples 20–28 indicate that all of the commercially available

TABLE II

| Material Tested (Example No.) | Quantity tested (mg) | Curing time (sec) | 24 hr. Results (% Lysis) | 48 hr. Results (% Lysis) | 72 hr. Results (% Lysis) |
|---|---|---|---|---|---|
| 7 (Run 1) | 25 | 0 | 100 | — | — |
|  | 20 | 0 | 0 | 0 | 30 |
|  | 15 | 0 | 20 | 100[a] | — |
| 7 (Run 2) | 25 | 0 | 0[b] | 30–40 | 80 |
|  | 20 | 0 | 0[b] | 40 | 85 |
|  | 15 | 0 | 0[b] | 5 | 5 |
| 8 | 35 | 20 | 0 | 0 | 0 |
|  | 35 | 30 | 0 | 0 | 0 |
| 9 | 25 | 0 | 100 | — | — |
|  | 20 | 0 | 100 | — | — |
|  | 15 | 0 | 100 | — | — |
| 9A | 35 | 20 | 100 | — | — |
|  | 35 | 30 | 100 | — | — |
| 10 | 250 | 0 | 0 | 0 | 0 |
|  | 150 | 0 | 0 | 0 | 0 |
| 11 | 250 | 40 | 0 | 0 | 0 |
|  | 150 | 40 | 0 | 0 | 0 |
| 12 | 200 | 0 | 0 | 0 | 0[b] |
|  | 100 | 0 | 0 | 0 | 0 |
| 13 | 200 | 40 | 0 | 0 | 0 |
|  | 100 | 40 | 0 | 0 | 0 |
| 14 | 200 | 0 | 0 | 0 | 0 |
|  | 100 | 0 | 0 | 0 | 0 |
| 15 | 200 | 40 | 0 | 0 | 0 |
|  | 100 | 40 | 0 | 0 | 0 |
| 16 | 200 | 0 | 0 | 0 | 0 |
| 17 | 200 | 0 | 0 | 0 | 0 |
| 18 | 200 | 5 min. | 0 | 0 | 0[b] |
| 19 | 100 | 0 | 40 | 100 | — |
| 20 | 100 | 0 | 35 | 100 | — |
| 21 | 200 | 5 min. | 30 | 10 | 20 |
| 22 | 100 | 0 | 100 | — | — |
| 23 | 100 | 0 | 100 | — | — |
| 24 | 200 | 5 min. | 100 | — | — |
| 25 | 200 | 0 | 100 | — | — |
| 26 | 200 | 40 | 70 | — | — |
| 27 | 200 | 0 | 0 | 5 | 20 |
| 28 | 200 | 40 | 0 | 0 | 0 |
| 29 | 200 | 0 | 0 | 0 | 0 |
| 30 | 200 | 0 | 0 | 0 | 0 |
| 31 | 200 | 0 | 0 | 0 | 0 |
| 32 | 250 | 40 | 60–70 | 100 | — |
|  | 150 | 40 | 5–10 | 5–10 | 50 |
| 33 | 250 | 0 | 100 | — | — |
|  | 150 | 0 | 100 | — | — |
| 34 | 200 | — | 0 | 0 | 0 |
| 35 | 15 | — | 100 | — | — |
| 36 | 35 | — | 0[b] | 0[b] | 0 |

[a]Severe reaction, cells fixed.
[b]Swelling of cells noted, no lysis. Slight intermediate response.

SUMMARY OF TABLE II

From the above Table II it can be seen that the uncured polymerizable composition of Example 7 (made using stannous octoate as the catalyst) is non-toxic after 72 hours using a test sample of 15 mg, and that when cured (Example 8) the composition is non-toxic using a 35 mg. test sample. On the contrary, the compositions of Examples 9 and 9A (the same compositions as Examples 7 & 8, respectively, except that DBTDL was used as the catalyst in place of S.O.) are toxic within 24 hours. In addition, it can be seen that polymerizable composite materials (Examples 10-15) and cements (Examples 16-18) made with the polymerizable HMPA-TMDI composite materials that were tested were found to be toxic, when uncured, within 72 hours.

Since the in vitro cell culture MEM test for cytotoxicity involves the incubation of cells in contact with toxins extracted from a test sample, it is quite possible to test a very small sample of a highly toxic material and observe only minimal cytotoxic effects (lysis). As a corollary, it is quite possible to test a very large sample of a relatively non-toxic material and observe a fairly high degree of cytotoxicity. Accordingly, for purposes of determining whether or not a polymerizable system is non-toxic and therefore within the scope of the present invention, the cell culture MEM test is to be performed using a sample size of 15 mg., 35 mg. or 200 mg., depending upon the relative amounts of "polymerizable material" and "calcium hydroxide plus filler" in the sample to be tested, and upon whether the sample is cured or uncured. The actual size of the test sample that should be used can be determined by referring to Table III, wherein the term "polymerizable material" includes all of the monomeric and prepolymeric materials, together with the initiator system, stabilizers, anti-oxidants, etc., and up to about 1% by weight of calcium hydroxide, calcium hydroxide former and fillers, combined. The term "calcium hydroxide plus filler" includes the combined amount of calcium hydroxide, calcium hydroxide former and filler.

TABLE III

| Composition of Sample % by weight | | Test Sample Size, Mg* | |
|---|---|---|---|
| | | Cured | Uncured |
| "Polymerizable Material" | 40-99 | 35 | 35 |
| "Ca(OH)$_2$ + filler" | 60-1 | | |
| "Polymerizable Material" | 0-39.9 | 200 | 200 |
| "Ca(OH)$_2$ + filler" | 100-60.1 | | |
| "Polymerizable Material" | 100 | 35 | 15 |

*for plural package self-cure systems, test "base", "catalyst" and mixture separately.

If sample sizes are used which are larger than those indicated in Table III, and non-toxic results are observed, the sample still can be deemed to be within the scope of the invention. If, however, larger size samples are observed to be toxic, the test is not conclusive and should be run again using sample of the size indicated in Table III. If sample sizes are used which are smaller than those stated above and toxic results are observed, the sample is outside the scope of the invention.

In order for a sample of the size indicated in Table III to be deemed non-toxic for the purpose of this invention, the % cell lysed or fixation after 72 hours must be less than 10%, and preferably should be zero. In preferred aspects of the invention, a 15 mg. sample of uncured, unfilled monomer or prepolymer would show no cell lyses after 72 hours, and in an even more preferred aspect, a 35 mg. sample of uncured, unfilled monomer or prepolymer would show less than 10% cell lyses after 72 hours. Cured samples always should show no observable lyses after 72 hours. In accordance with the foregoing test procedure requirements, it will be seen that certain of the compositions of Examples 1-36 pass the cytotoxicity test and, thus, are within the scope of the invention, while others fail the test and are outside the scope of the invention. The pass/fail results of the compositions of Examples 1-36, which were tested using an appropriate sample size, are set forth in Table IV.

TABLE IV

| PASS OR FAIL CYTOTOXICITY TEST | | | | |
|---|---|---|---|---|
| Material Tested Example No. | Sample Size (mg.) | Curing Time (sec.) | 72 hr results (% lyses) | Pass (P) or Fail (F) |
| 1 | 20 | 0 | 0 | P |
| | 15 | 0 | 0 | P |
| 2 | 29 | 0 | 100$^a$ | F |
| | 20 | 0 | 100$^a$ | F |
| | 3 | 0 | 100$^a$ | F |
| 3 | 25 | 0 | 100 | F |
| | 2 | 0 | 100 | F |
| 7 | 15 | 0 | 5 | P |
| 9 | 25 | 0 | 100 | F |
| | 20 | 0 | 100 | F |
| | 15 | 0 | 100 | F |
| 10 | 250 | 0 | 0 | P |
| 12 | 200 | 0 | 0$^b$ | P |
| 14 | 200 | 0 | 0 | P |
| 16 | 200 | 0 | 0 | P |
| 17 | 200 | 0 | 0 | P |
| 18 | 200 | 0 | 0 | P |
| 19 | 100 | 0 | 100 | F |
| 20 | 100 | 0 | 100 | F |
| 22 | 100 | 0 | 100 | F |
| 23 | 100 | 0 | 100 | F |
| 25 | 200 | 0 | 100 | F |
| 27 | 200 | 0 | 20 | F |
| 30 | 200 | 0 | 0 | P |
| 31 | 200 | 0 | 0 | P |
| 33 | 250 | 0 | 100 | F |
| | 150 | 0 | 100 | F |
| 11 | 250 | 40 | 0 | P |
| 13 | 200 | 40 | 0 | P |
| 15 | 200 | 40 | 0 | P |
| 21 | 200 | 5 min. | 20 | F |
| 24 | 200 | 5 min. | 100 | F |
| 26 | 200 | 40 | 70 | F |
| 28 | 200 | 40 | 0 | P |
| 32 | 250 | 40 | 100 | F |
| | 150 | 40 | 50 | F |
| 34 | 200 | 0 | 0 | P |
| 35 | 15 | — | 100 | F |
| 36 | 35 | — | 0$^b$ | P |

It will be evident that those materials in Table IV which fail the cytotoxicity test are outside the scope of the invention claimed herein.

EXAMPLE 37

Histological Response In Primates

The histological response of pulpal tissue toward the visible light cure composition of Example 1 was determined by means of tests performed on eighty four Class V cavity preparations cut in incisors, premolars and molars of three *Cynomolgus Fascicularis*. The majority of the cavity preparations were such as to require pulp protection against chemical insult, or stimulation to form secondary dentin. Half of the teeth were prepared such that the remaining dentin thickness was +1 mm. The other half of the teeth were prepared until an exposure, as evidenced by the presence of blood, was accomplished. The prepared teeth were filled with the calcium hydroxide containing composition and cured by exposure from a Prisma-Lite ® light curing unit for 20 seconds. One animal was sacrificed after 4 days, the other two after 67 days. After jaw dissection, the apices were removed at ⅓ height, to allow better fixation in 10% neutral buffered formalin. The specimens were further processed for routine histological evaluation. Pulpal exposed or non-exposed teeth. Responses of 0.5–1.0 occurred in four of 18 exposed samples; a response of zero indicating no inflammation, and a response of 1 indicating mild irritation. (See page 1512 of H. R. Stanley et al., *Compatibility of Various Materials with Oral Tissues II: Pulp Response to Composite Ingredients*, J. Dent. Res., 58(5), pp. 1507–1517 (May, 1979). No chemical mummification was seen. On recut 67 day specimens, 19 were found to have pulp exposures. Of these 19 exposures, 11 specimens were found to exhibit excellent bridge formation due to stimulation of secondary dentin over the exposures and 6 specimens were found to exhibit good bridge formation due to secondary dentin over the exposures. The inflammatory reactions that were noted were related to emboli of the visible light curing calcium hydroxide containing composition, or impaction of the composition's particles. The results of the tests indicated that the composition of Example 1 met the acceptable histological requirements in primates.

The visible light curable dental materials of the present invention in a preferred form are comprised of calcium hydroxide and barium sulfate fillers dispersed in a non-toxic polymerizable monomer or prepolymer along with a small quantity of initiator and accelerator. When exposed to the visible light delivered by a Prisma-Lite®, a product of Dentsply International Inc., for 10-20 seconds, the preferred products of this example cure to a depth of 1 mm thick to show a desirable basicity of about pH 10. The physical properties of the cured materials are superior to any calcium hydroxide containing cavity liners known until this time, and both the uncured and cured materials are biologically compatible. In vitro tissue culture MEM cytotoxicity tests, acute stystemic toxicity, Ames, Muscle implantation tests, and in vivo *Cynomolgus Fascicularis* (primate) tests all show that the present materials are non-toxic and assist reparative dentin formation. The low water solubility and high acid resistance of the cured material permits retention of the cured material's physical properties such as compressive strength. The improved novel materials may be made radiopaque for dental diagnostic purposes and are compatible with all standard dental restorative materials.

It should be understood that the present invention is intended to provide tissue compatible materials especially useful in dentistry that are not only non-toxic in their cured state but also in their uncured and curing states. The uncured material may be in prolonged contact with tissue as uncured material either because of spillage or because of failure of completion of the curing process. In addition, the curing procedure itself can cause toxicity, for example, by creation of intermediate highly toxic materials. It is a preliminary belief that the polymeric system of the present invention without calcium hydroxide may stimulate the formation of secondary dentin or provide permanent non-toxic, friendly protection to the dentin regardless of secondary dentin formation.

It should be apparent that the foregoing description and examples illustrate preferred embodiments of the invention and that the concepts employed may, based upon such description and examples, be employed in other embodiments without departing from the scope of the invention. Accordingly, the following claims are intended to protect the invention broadly, as well as in the specific forms set forth herein.

What is claimed is:

1. A method of treating living pulpal tissue comprising the steps of:
    contacting living pulpal tissue with a polymerizable composition that is polymerizable in situ by a mechanism other than chelation or saponification, said composition comprising at least one polymerizable monomer or prepolymer component, a curing component for said polymerizable monomer or prepolymer component, and calcium hydroxide or calcium oxide or mixtures thereof, said monomer or prepolymer component, as well as said composition, being substantially non-toxic toward said pulpal tissue, both before and after said composition is polymerized, said non-toxicity being observable by in vitro cell culture bicompatibility testing utilizing monolayers of mouse fibroblast cells (1929 or equivalent) in a growth medium consisting of 5% bovine serum solution in Minium Essential Medium (MEM) or by in vivo histological response testing using prepared teeth of a primate; and polymerizing said composition in situ.

2. The method of claim 1, wherein said polymerizable composition comprises at least one polymerizable ethylenically unsaturated monomer or prepolymer, and a catalytically effective amount of a free radical initiator system; and wherein said composition is polymerized in situ by free radical initiation.

3. The method of claim 2, wherein said free radical initiator system comprising a photoinitiator system.

4. The method of claim 3 wherein said photoinitiator system is operative in response to exposure to visible light.

5. The method of claim 2, wherein said polymerizable composition comprises from about 45 to about 90% by weight of filler selected from the group consisting of colloidal silica, fused quartz, aluminum oxide, ceramic beads, glass beads, calcium phosphates, metal silicates and aluminosilicates and mixtures thereof.

6. The method of claim 4, wherein said photoinitiator system comprises an α-diketone and a reducing agent which is capable of reducing said α-diketone when the latter is in an excited state.

7. The method of claim 2, wherein said free radical initiator system comprises a photoinitiator system operative in response to exposure to visible light.

8. The method of claim 7, wherein said polymerizable composition comprises from about 45 to about 90% by weight of filler selected from the group consisting of colloidal silica, fused quartz, aluminum oxide, ceramic beads, glass beads, calcium phosphates, metal silicates and aluminosilicates and mixtures thereof.

9. The method of claim 7, wherein said photoinitiator system comprises an α-diketone, and a reducing agent which is capable of reducing said α-diketone when the latter is in an excited state.

10. The method of claim 7, wherein said free radical initiator system comprises a photoinitiator system operative upon exposure to light having a wavelength in the range of from about 360 to about 550 nm.

11. The method of claim 7, wherein said free radical initiator system comprising from about 0.01 to about 5% by weight of α-diketone and from about 0.1 to about 5% by weight of amine, and wherein said composition is in the form of a shelf-stable one package system prior to use.

12. The method of claim 11, further comprising radiopaque filler in an amount sufficient to render said composition radiopaque.

13. The method of claim 2, wherein said at least one polymerizable ethylenically unsaturated monomer or prepolymer comprises at least one polymerizable vinyl urethane derived from a member selected from the group consisting of adducts of organic diisocyanates or isocyanate-terminated urethane prepolymers and an ethylenically unsaturated compound having hydroxyl functionality and adducts of hydroxyl terminated prepolymers or organic polyols and an ethylenically unsaturated compound having isocyanato functionality.

14. The method of claim 13, wherein said ethylenically unsaturated compound having hydroxyl functionality is a member selected from the group consisting of esters of acrylic or methacrylic acid and a hydroxy alkanol of at least two carbon atoms.

15. The method of claim 13, wherein said polymerizable vinyl urethane prepolymer is selected from the group consisting of prepolymers derived from hexamethylene diisocyanate and hydroxypropyl (meth)acrylate, from trimethyl hexamethylene diisocyanate and hydroxypropyl (meth)acrylate, from the reaction product of methylene-bis-(4-cyclohexyl isocyanate) and a polytetramethylene ether glycol with hydroxypropyl (meth)acrylate, and mixtures thereof.

16. The method of claim 7, wherein said at least one polymerizable ethylenically unsaturated monomer or prepolymer comprises at least one polymerizable vinyl urethane derived from a member selected from the group consisting of organic diisocyanates or isocyanate-terminated urethane prepolymers and an ethylenically unsaturated compound having hydroxyl functionality and adducts of hydroxyl terminated prepolymers or organic polyols and an ethylenically unsaturated compound having isocyanato functionality.

17. The method of claim 16, wherein said ethylenically unsaturated compound having hydroxyl functionality is a member selected from the group consisting of esters of acrylic or methacrylic acid and a hydroxy alkanol of at least two carbon atoms.

18. The method of claim 16, wherein said polymerizable vinyl urethane prepolymer is selected from the group consisting of prepolymers derived from hexamethylene diisocyanate and hydroxypropyl (meth)acrylate, from trimethyl hexamethylene diisocyanate and hydroxypropyl (meth)acrylate, from the reaction product of methylene-bis-(4-cyclohexyl isocyanate) and a polytetramethylene ether glycol with hydroxypropyl (meth)acrylate, and mixtures thereof.

19. The method of claim 16, wherein said polymerizable vinyl urethane is characterized by the structural formula wherein $R_1$ and $R_5$, independently, are H, alkyl or substituted alkyl; $R_2$ and $R_4$, independently, are alkylene, substituted alkylene, cycloalkylene, substituted cycloalkylene, arylene, or substituted arylene; and $R_3$ is alkylene, substituted alkylene, cycloalkylene, substituted cycloalkylene, arylene, substituted arylene, heterocyclic, substituted heterocyclic, the reaction product of an organic diisocyanate or an isocyanate terminated prepolymer and a compound having hydroxyl functionality, or the reaction product of a polyol or a hydroxyl terminated prepolymer and a compound having isocyanato functionality.

20. The method of claim 19, wherein $R_1$ and $R_5$, independently, are H or $C_1-C_4$ alkyl; $R_2$ and $R_4$, independently, are $C_1-C_6$ alkylene; and $R_3$ is $C_1-C_6$ alkylene, $C_2-C_{12}$ substituted alkylene, or the reaction product of an organic diisocyanate or polyisocyanate with an alkanol or polyalkanol.

21. The method of claim 13, wherein said at least one polymerizable ethylenically unsaturated monomer or prepolymer comprises a mixture of at least one polymerizable vinyl urethane prepolymer and at least one ester of acrylic acid or methacrylic acid.

22. The method of claim 21, wherein said at least one ester of acrylic acid or methacrylic acid is a member selected from the group consisting of a diacrylate, a dimethacrylate, a polyacrylate and a polymethacrylate, and mixtures thereof.

23. The method of claim 22, wherein said at least one ester of acrylic acid or methacrylic acid is triethylene glycol dimethacrylate.

24. The method of claim 23, wherein said vinyl urethane is selected from the group consisting of vinyl urethanes derived from hexamethylene diisocyanate and hydroxypropyl methacrylate, from trimethyl hexamethylene diisocyanate and hydroxypropyl methacrylate, from the reaction product of methylene-bis-(4-cyclohexyl isocyanate) and a polytetramethylene ether glycol with hydroxypropyl (meth)acrylate, and mixtures thereof.

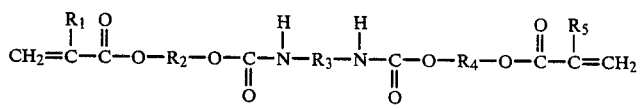

* * * * *